United States Patent [19]

Bledsoe

[11] Patent Number: 4,463,751
[45] Date of Patent: Aug. 7, 1984

[54] STABILIZING KNEE HINGE

[76] Inventor: Gary R. Bledsoe, 2001 Kent Dr., Arlington, Tex. 76010

[21] Appl. No.: 453,716

[22] Filed: Dec. 27, 1982

[51] Int. Cl.$^3$ ............................................. A61F 3/00
[52] U.S. Cl. .................................... 128/80 C; 128/88; 3/22
[58] Field of Search .................... 128/80 C, 87 R, 88; 3/22

[56] References Cited

U.S. PATENT DOCUMENTS

| 3,030,634 | 4/1962 | Bair | 128/88 X |
|---|---|---|---|
| 4,340,041 | 7/1982 | Frank | 128/80 C |
| 4,353,361 | 10/1982 | Foster | 128/88 |

*Primary Examiner*—John D. Yasko
*Attorney, Agent, or Firm*—Hubbard, Thurman, Turner & Tucker

[57] ABSTRACT

A stabilizing knee hinge which can be utilized in conjunction with a brace for bracing or casting the human knee. The hinge simulates the movement of the human knee and can be utilized to restrict the range of motion of the knee to any desired range or to completely immobilize the knee joint. The hinge includes a femoral joint element which has two plates secured in a fixed parallel relationship. Two arcuate cam slots are formed through both plates. A pair of generally circular stop limit plates are rotatably mounted within the two femoral joint element plates and may be independently rotated to intersect the arcuate cam slots. A first stop limit plate rotates in one direction to set the stop limit for knee extension and the second stop limit plate rotates in the other direction to set the stop limit for knee flexion. A set screw is provided to fix the position of the stop limit plates as desired. The tibial joint element includes a second pair of plates which are secured in a fixed parallel relationship and which are disposed outside of the femoral joint element plates. A pair of pivot and bearing pins couple the tibial and femoral joint element plates through the arcuate cam slots in the femoral joint element plates. The tibial joint element is then free to rotate with respect to the femoral joint element in a composite arc defined by the arcuate cam slots and the position of the stop limit plates.

10 Claims, 5 Drawing Figures

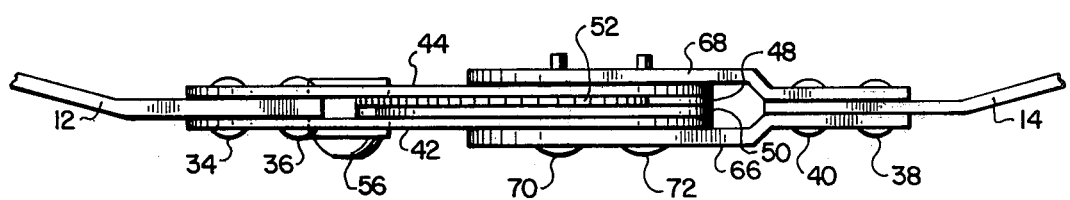
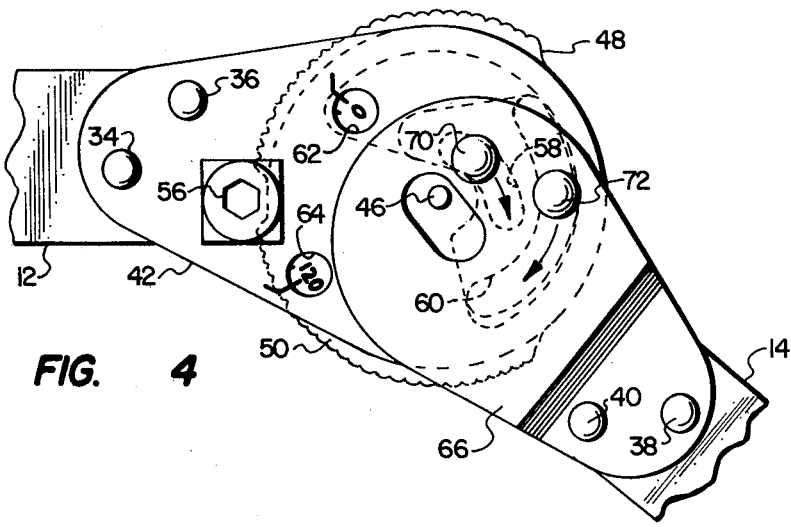
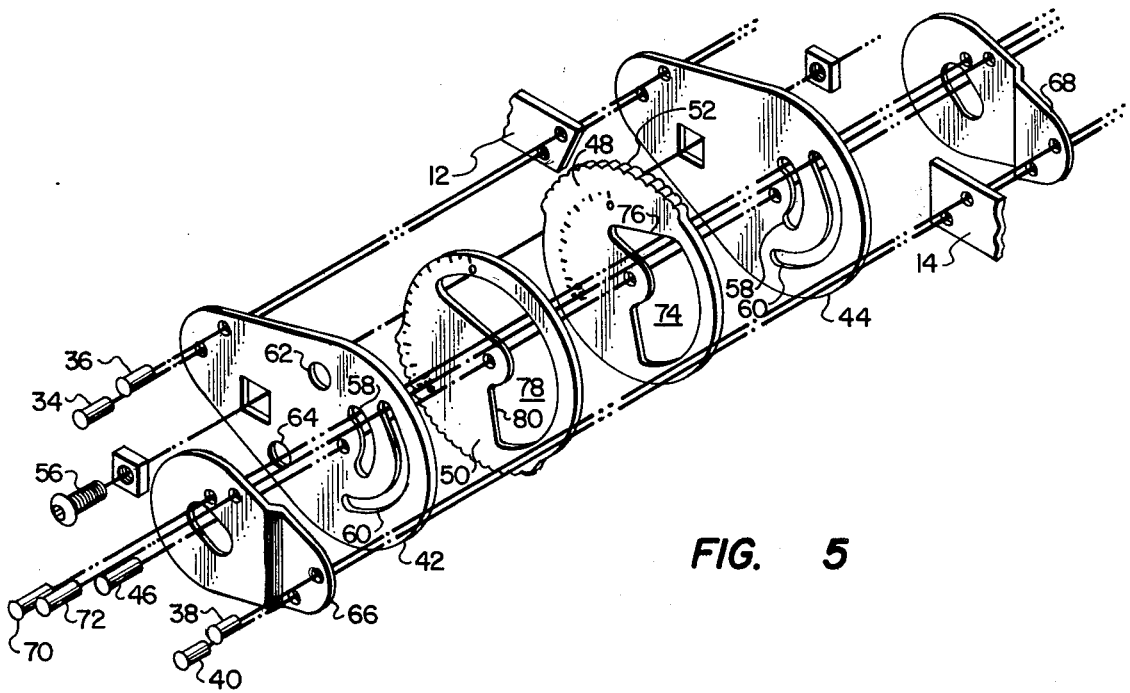

STABILIZING KNEE HINGE

BACKGROUND OF THE INVENTION

This invention relates in general to hinges for stabilizing the human knee and in particular to stabilizing knee hinges which simulate the movement of the human knee and which can be utilized to restrict the range of motion of the knee to any desired range or to completely immobilize the knee joint.

Knee joint braces and hinges are well known in the prior art. Such devices are typically utilized for treating fractures, re-education therapy of arthrolysis, orthopedic treatment of limbs after surgical correction, early re-education therapy of ligamentous lesions and to provide restraining articulated orthoses for traumatic knee lesions and other athletic knee injuries.

Generally, the splint or brace which utilizes a knee stabilizing hinge is constructed utilizing two identical side members each of which includes a femoral and tibial section, which are then fastened to the leg by means of straps or alternatively, fastened to a plaster or fiberglass cast.

The difficulty associated with the design of a stabilizing knee hinge is due to the complexity of the knee joint. Unlike the simpler hinge joints of the body, the knee joint has an axis of rotation which moves over a curve that is well defined and difficult to implement in a mechanical hinge. Recently, the manufacturers of such devices have begun to manufacture a so-called "polycentric" hinge which attempts to duplicate the motion of the knee utilizing gear and mechanically coupled dual pivots.

While representing an advance over the prior art, theses hinges have several shortcomings. Typically these hinges are too flexible to prevent hyperextension of the knee joint or too rigid to permit therapy. Additionally, the desirable aspect of restricting the range of motion of the knee utilizing a geared hinge is quite difficult. Several examples of knee hinges are known in the prior art. U.S. Pat. No. 4,340,041, issued to F. Frank, discloses an articulated knee splint which includes two anchor bars which may be locked, by means of a lock plate, into a desired angular position.

U.S. Pat. No. 4,337,764 discloses a knee joint brace which incorporates a "polycentric" hinge which includes an arcuate groove with two adjustable stop pins to permit a variation in the amount of flexion permitted. A second hinge below the adjustable hinge is utilized to simulate the motion of the human knee.

U.S. Pat. No. 4,088,130, issued to L.T. Applegate, discloses a simple lockable hinge which may be utilized to restrict the range of motion of the knee to a desired arc; however, there is no provision in Applegate to simulate the complex motion of the human knee.

U.S. Pat. No. 3,826,251 discloses a knee hinge that utilizes two slots to simulate the knee motion. A straight vertical slot and an arcuate slot are provided to demonstrate the pivot and slide motion of the knee. The arcuate slot includes a detent to permit the leg to be locked in the rigid position for prolonged standing.

Finally, U.S. Pat. No. 3,779,654 discloses an artificial knee joint which utilizes two arcuate cam surfaces to simulate the natural knee motion. There is no provision in this joint however for the restriction of the range motion of the knee.

SUMMARY OF THE INVENTION

Accordingly, it is one object of the present invention to provide an improved stabilizing knee hinge.

It is another object of the invention to provide an improved stabilizing knee hinge which simulates the motion of the human knee.

It is yet another object of the present invention to provide an improved stabilizing knee hinge which may be utilized to limit the range of motion of the human knee.

It is another object of the present invention to provide an improved stabilizing knee hinge which may be utilized to immobilize the knee.

It is yet another object of the present invention to provide an improved stabilizing knee hinge which is adjustable and sufficiently sturdy to endure repetitive use.

The foregoing objects are achieved as is now described. The novel hinge of the present invention includes a femoral joint element which has two plates secured in a fixed parallel relationship. Two arcuate cam slots are formed through both plates. A generally circular pair of stop limit plates are rotatably mounted within the two femoral joint element plates and may be independently rotated to intersect the arcuate cam slots. A first stop limit plate rotates in one direction to set the stop limit for knee extension and the second stop limit plate rotates in the other direction to set the stop limit for knee flexion. A set screw is provided to fix the position of the stop limit plates as desired. The tibial joint element includes a second pair of plates which are secured in a fixed parallel relationship and which are disposed outside of the femoral joint element plates. A pair of pivot and bearing pins couple the tibial and femoral joint element plates through the arcuate cam slots in the femoral joint element plates. The tibial joint element is then free to rotate with respect to the femoral joint element in a composite arc defined by the arcuate cam slots and the position of the stop limit plates.

BRIEF DESCRIPTION OF THE DRAWINGS

The novel features believed characteristic of the invention are set forth in the appended claims. The invention itself; however, as well as a preferred mode of use, further objects and advantages thereof, will best be understood by reference to the following detailed description of an illustrative embodiment when read in conjunction with the accompanying drawings, wherein:

FIG. 3 depicts a side view of the novel stabilizing knee hinge of FIG. 2;

FIG. 4 depicts a top view of the novel stabilizing knee hinge of FIG. 2 in a flexed position; and FIG. 5 depicts an exploded view of the novel stabilizing knee hinge of FIG. 2.

DETAILED DESCRIPTION OF THE INVENTION

Figure 1:
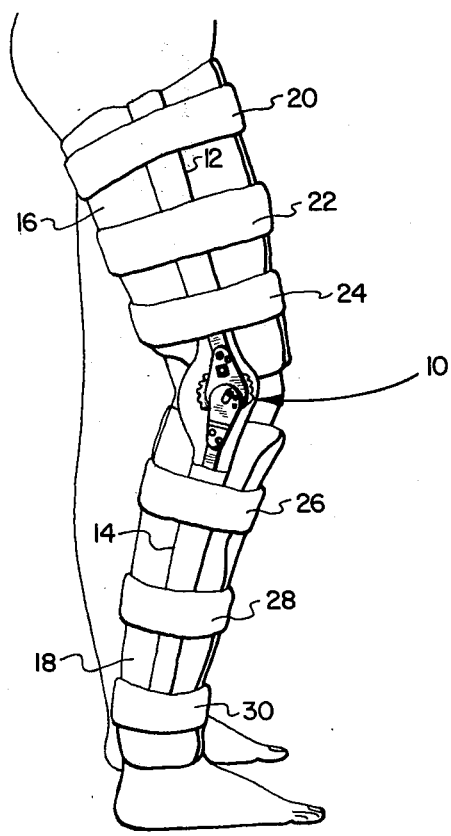
FIG. 1 depicts a side view of a leg brace system incorporating the novel stabilizing knee hinge of the present invention.
Figure 2:
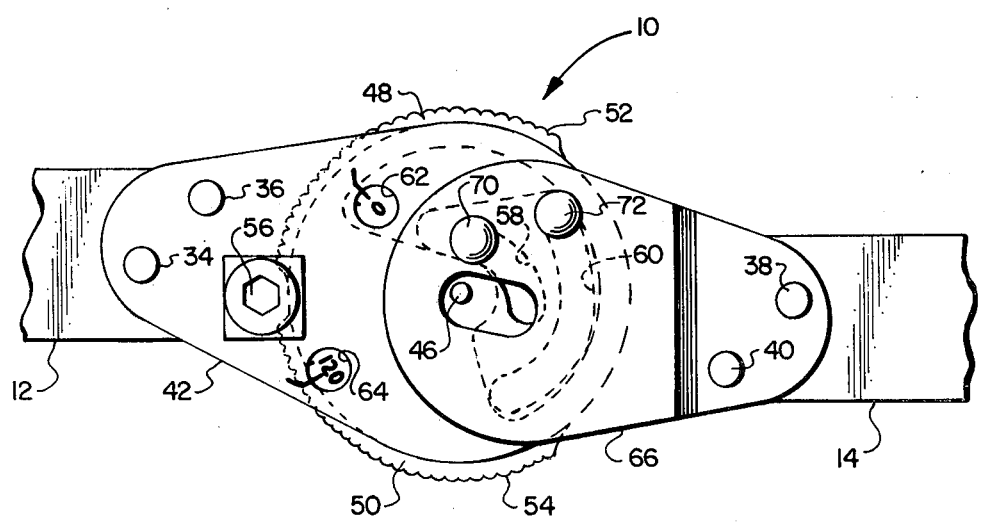
FIG. 2 depicts a top view of the novel stabilizing knee hinge of the present invention in the fully extended position.

With reference now to the figures, and in particular with reference to FIG. 1, there is depicted a side view of a leg brace system which incorporates the novel stabilizing knee hinge 10 of the present invention. Knee hinge 10 is fixedly coupled to elongated rigid femoral and tibial arms 12 and 14, respectively. Those skilled in the art will appreciate that leg brace systems of the type illustrated typically include rigid medial arms as well as the lateral arms depicted and that in such systems two stabilizing knee hinges will be needed. The remainder of the leg brace consists of a pair of rigid posterior supports 16 and 18 and a plurality of straps 20, 22, 24, 26, 28 and 30 which serve to fasten the femoral arm and tibial arm to the leg and supports. Of course, the brace may include anterior bracing plates, such as a tibial bracing plate or femoral bracing plate. Additionally, the brace can include shoe inserts or apparatus to permit it to be utilized as a walking brace. The skilled practitioner in this area will also recognize that femoral arm 12 and tibial arm 14 may be mounted to a plaster or a fiberglass cast. Referring now to FIG. 2, there is depicted a top view of hinge 10 of the present invention. As can be seen, hinge 10 is fixedly mounted to femoral arm 12 and tibial arm 14 by means of rivets 34, 36, 38 and 40, although hinge 10 may be fastened to femoral arm 12 and tibial arm 14 by any method well known in the art such as welding.

Beginning a femoral arm 12, hinge 10 includes femoral plates 42 and 44 (not depicted) which are mounted in spaced parallel relationship. Rotatably mounted between femoral plates 42 and 44 by means of pivot 46 are generally circular stop limit plates 48 and 50. Stop limit plate 48 includes a knurled raised portion 52 and, as can be seen in FIG. 2, may be rotated in a clockwise position from the position depicted. Similarly, stop limit plate 50 includes a knurled raised portion 54 and may be rotated in a counterclockwise direction from the position depicted. Set screw 56 is utilized to restrict the rotation of stop limit plates 48 and 50 and also prevents reverse rotation beyond the point at which each knurled raised portion intersects set screw 56.

Femoral plates 42 and 44 also both include two arcuate cam slots 58 and 60 which serve to implement the polycentric aspect of the human knee. Arcuate cam slot 58 determines the actual angle of the hinge at any point and arcuate cam slot 60 determines the length of the hinge at each point. Arcuate cam slots 58 and 60 are designed to closely simulate the actual movement of the human knee when the brace is fitted properly, that is, when pivot 46 exactly overlays the femoral epicondyl. Additionally, only femoral plate 42 includes aperture 62 and 64 which permit the physician or therapist to see angular indicia on stop limit plates 48 and 50 as illustrated. As should be obvious, such apertures are not necessary on femoral plate 44 since that plate will be against the body of the wearer during adjustment.

Completing hinge 10, tibial plates 66 and 68 (not shown) are mounted in spaced parallel relationship outside of femoral plates 42 and 44. Pivot and bearing pins 70 and 72 are mounted to arcuate cam slots 58 and 60 respectively and serve to pivotally mount tibial plates 66 and 68 to femoral plates 42 and 44. Thus, the pivoting of tibial arm 14 will cause pivot and bearing pins 70 and 72 to track clockwise to arcuate cam slots 58 and 60, permitting tibial plates 66 and 68 to pivot with respect to femoral plates 42 and 44.

With reference now to FIG. 3, there is depicted a top view of hinge 10 of FIG. 2 which clearly illustrates the arrangement of femoral plates 42 and 44 with stop limit plates 48 and 50 disposed therebetween. Additionally, tibial plates 66 and 68 can be see mounted outside of femoral plates 42 and 44.

Referring now to FIG. 4, there is depicted hinge 10 in a slightly angled configuration, showing the action of pivot and bearing pins 70 and 72 in arcuate cam slots 58 and 60. Those skilled in the art will appreciate that this twin cam approach will permit an excellent approximation of the motion of the human knee. The range of motion of pivot and bearing pins 70 and 72, if unrestricted by stop limit plates 48 and 50, will permit 120 degrees of flexion and extension in the depicted embodiment, although a greater or lesser range of motion may be selected as a matter of design choice. The operation of stop limit plates 48 and 50 may be utilized to restrict or eliminate totally the range of motion of pivot and bearing pins 70 and 72 in a manner which may be best understood upon reference to FIG. 5.

FIG. 5 depicts an exploded view of stabilizing knee hinge 10 of the present invention. Of particular interest in FIG. 5 is the method of operation of stop limit plates 48 and 50. As can now be seen clearly, stop limit plate 48 is a generally circular plate which includes knurled raised surface 52 and a large cutaway section 74. Section 74 includes an edge section 76 which, upon clockwise rotation of stop limit plate 48, can be rotated into a position which intersects arcuate cam surfaces 58 and 60, thus limiting the counterclockwise movement of pivot and bearing pins 70 and 72 therein. Similarly, stop limit plate 50 includes a cutaway section 78 and edge section 80 which may be rotated in a counterclockwise direction into a position which intersects arcuate cam surfaces 58 and 60, thus limiting the clockwise movement of pivot and bearing pins 70 and 72 therein. Cutaway section 78 can be seen to be a great deal larger than cutaway section 74; however, those skilled in the art will recognize that this will permit the angular indicia engraved on stop limit plate 48 to be visible through cutaway section 78 and aperture 62 of femoral plate 42, since stop limit plate 48 underlies stop limit plate 50.

Having observed the operation of stop limit plates 48 and 50, it should be apparent that hinge 10 may be adjusted to permit movement through any limited range of motion or, in the alternative, stop limit plates 48 and 50 may both be rotated into contact with pivot and bearing pins 70 and 72 to immobilize pins 70 and 72 in any desired position.

Each of the components of hinge 10 is preferably constructed of a rigid, high tensile strength material such as steel, and each will withstand repetitive utilization without failure, thus saving considerable over known hinge systems which must be renewed fairly often. Additionally, hinge 10 of the present invention permits the attending physician or therapist to simply and accurately "dial" the range of motion desired for a particular application.

Although the invention has been described with reference to a specific embodiment, this description is not meant to be construed in a limiting sense. Various modifications of the disclosed embodiment as well as alternative embodiments of the invention will become apparent to persons skilled in the art upon reference to the description of the invention. It is therefore contemplated that the appended claims will cover any such modifications or embodiments that fall within the true scope of the invention.

What is claimed is:

1. A knee stabilizing hinge for simulating the motion of the human knee and for restricting the range of motion thereof, said hinge comprising:

a first joint element including a first pair of plates secured in spaced parallel relationship including at least one arcuate cam slot formed through said first pair of plates;

a second pair of plates rotatably mounted between said first pair of plates, each of said second pair of plates rotatable independently of the other and including a stop limit selectively rotatable into intersection with said at least one arcuate cam slot;

means for selectively restricting the rotation of both of said second pair of plates with respect to said first pair of plates;

a second joint element including a third pair of plates secured in spaced parallel relationship enclosing and rotatable about at least a portion of said first pair of plates; and a pivot and bearing means mounted to each of said third pair of plates through said at least one arcuate cam slot, said pivot and bearing means engagable with said at least one arcuate cam slot and movable therein to the extent permitted by the position of said stop limits.

2. The knee stabilizing hinge according to claim 1 wherein the stop limit of a first of said second pair of plates is rotated clockwise into intersection with said at least one arcuate cam slot and wherein the stop limit of a second of said second pair of plates is rotatable counterclockwise into intersection with said at least one arcuate cam slot.

3. The knee stabilizing hinge according to claim 2 wherein said stop limits are both rotatable into contact with said pivot and bearing means whereby the movement of said pivot and bearing means is completely restricted.

4. The knee stabilizing hinge according to claim 2 wherein one of said first pair of plates includes at least one aperture to permit viewing of said second pair of plates and wherein said second pair of plates includes indicia indicative of the amount of angular rotation of said second pair of plates with respect to said first pair of plates.

5. The knee stabilizing hinge according to claim 1 wherein said first and second joint elements both include elongated members adapted to secure said knee stabilizing hinge to an orthopedic knee brace.

6. A knee stabilizing brace for simulate motion of the human knee and for restricting the range of motion thereof, said hinge comprising:

a first joint element including a first pair of plates secured in spaced parallel relationship, including first and second arcuate cam slots formed through said first pair of plates, said first and second arcuate cam slot each having a different radius of curvature;

a second pair of plates rotatably mounted between said first pair of plates, each of said second pair of plates rotatable independently of the other and including a stop limit selectively rotatable into intersection with said first and second arcuate cam slots;

means for selectively restricting the rotation of both of said second pair of plates with respect to said first pair of plates;

a second joint element including a third pair of plates secured in spaced parallel relationship enclosing and rotatable about at least a portion of said first pair of plates;

a first pivot and bearing means mounted to each of said third pair of plates through said first arcuate cam slot, said first pivot and bearing means engagable with said first arcuate cam slot and movable therein to the extent permitted by the position of said stop limits; and a second pivot and bearing means mounted to each of said third pair of plates through said second arcuate cam slot, said second pivot and bearing means engagable with said second arcuate cam slot and movable therein to the extent permitted by the position of said stop limits.

7. The knee stabilizing hinge according to claim 6 wherein the stop limit of a first of said second pair of plates is rotated clockwise into intersection with said at least one arcuate cam slot and wherein the stop limit of a second of said second pair of plates is rotatable counterclockwise into intersection with said at least one arcuate cam slot.

8. The knee stabilizing hinge according to claim 7 wherein said stop limits are both rotatable into contact with said first and second pivot and bearing means whereby the movement of first and second pivot and bearing means is completely restricted.

9. The knee stabilizing hinge according to claim 6 wherein one of said first pair of plates includes at least one aperture to permit viewing of said second pair of plates and wherein said second pair of plates includes indicia indicative of the amount of angular rotation of said second pair of plates with respect to said first pair of plates.

10. The knee stabilizing hinge according to claim 6 wherein said first and second joint elements both include elongated members adapted to secure said knee stabilizing hinge to an orthopedic knee brace.

* * * * *